United States Patent
Milos et al.

(10) Patent No.: US 11,719,644 B2
(45) Date of Patent: Aug. 8, 2023

(54) THERMOLUMINESCENT COMPOSITE PARTICLE AND MARKING COMPRISING SAME

(71) Applicant: SICPA HOLDING SA, Prilly (CH)

(72) Inventors: Mia Milos, Morges (CH); Xavier Cédric Raemy, Belmont-sur-Lausanne (CH); Jean-Luc Dorier, Bussigny (CH)

(73) Assignee: SICPA HOLDING SA, Prilly (CH)

( * ) Notice: Subject to any disclaimer, the term of this patent is extended or adjusted under 35 U.S.C. 154(b) by 19 days.

(21) Appl. No.: 14/577,390

(22) Filed: Dec. 19, 2014

(65) Prior Publication Data

US 2015/0177153 A1  Jun. 25, 2015

Related U.S. Application Data

(60) Provisional application No. 61/919,037, filed on Dec. 20, 2013.

(30) Foreign Application Priority Data

Dec. 20, 2013  (WO) ................ PCT/EP2013/077823

(51) Int. Cl.
*G01N 21/71* (2006.01)
*C09K 11/68* (2006.01)
(Continued)

(52) U.S. Cl.
CPC ............ *G01N 21/71* (2013.01); *C01G 49/08* (2013.01); *C09K 9/00* (2013.01); *C09K 11/02* (2013.01); *C09K 11/681* (2013.01); *C09K 11/77* (2013.01); *C09K 11/7746* (2013.01); *G01N 33/02* (2013.01); *G01N 33/15* (2013.01); *C01P 2002/50* (2013.01); *C01P 2004/32* (2013.01);
(Continued)

(58) Field of Classification Search
CPC .......... G01N 21/6428; G01N 21/6458; G01N 21/64; G01N 21/6408; G01N 2021/6421
See application file for complete search history.

(56) References Cited

U.S. PATENT DOCUMENTS 4,849,639 A    7/1989  Born et al.
5,683,179 A *  11/1997 Lowry ........................ 374/17
(Continued)

FOREIGN PATENT DOCUMENTS

CN    102446451    5/2012
GB    2427157      12/2006
(Continued)

OTHER PUBLICATIONS

Eeckhout et al. "Persistent Luminescence in Non-Eu2+-Doped Compounds: A Review", Materials 2013, p. 2789-2818 (Year: 2013).*

(Continued)

*Primary Examiner* — David P Porta
*Assistant Examiner* — Mamadou Faye
(74) *Attorney, Agent, or Firm* — Muncy, Geissler, Olds & Lowe, P.C.

(57) ABSTRACT

Disclosed is a composite particle for use in a marking that is suitable for identification/authentication purposes. The particle comprises at least one superparamagnetic portion and at least one thermoluminescent portion and optionally also a thermoconductive portion between the superparamagnetic and thermoluminscent portions.

26 Claims, 2 Drawing Sheets

(51) Int. Cl.

| | |
|---|---|
| *C01G 49/08* | (2006.01) |
| *C09K 11/77* | (2006.01) |
| *C09K 11/02* | (2006.01) |
| *C09K 9/00* | (2006.01) |
| *G01N 33/02* | (2006.01) |
| *G01N 33/15* | (2006.01) |

(52) U.S. Cl.
CPC ...... *C01P 2004/34* (2013.01); *C01P 2004/64* (2013.01); *C01P 2004/80* (2013.01); *G01N 2201/061* (2013.01); *G01N 2201/067* (2013.01); *G01N 2201/08* (2013.01); *Y10T 428/13* (2015.01); *Y10T 428/24893* (2015.01)

(56) References Cited

U.S. PATENT DOCUMENTS

| | | | | |
|---|---|---|---|---|
| 6,287,993 | B1* | 9/2001 | Fu et al. | 501/5 |
| 9,617,435 | B2* | 4/2017 | Krueger | C09D 7/69 |
| 2003/0013593 | A1* | 1/2003 | Beall et al. | 501/10 |
| 2003/0215825 | A1* | 11/2003 | Tong | G01N 33/54313 436/526 |
| 2004/0101822 | A1* | 5/2004 | Wiesner | C09K 11/06 435/7.1 |
| 2005/0096420 | A1* | 5/2005 | Delp | C08K 3/22 524/439 |
| 2005/0120917 | A1* | 6/2005 | Ruger | C09C 1/0015 106/415 |
| 2005/0208539 | A1* | 9/2005 | Vann | C12Q 1/686 435/6.16 |
| 2006/0140871 | A1* | 6/2006 | Sillerud | B82Y 5/00 977/930 |
| 2006/0142419 | A1 | 6/2006 | Xu et al. | |
| 2007/0087195 | A1* | 4/2007 | Meyer | C09K 11/02 428/323 |
| 2007/0190298 | A1* | 8/2007 | Hampden-Smith | B42D 25/29 428/204 |
| 2007/0275244 | A1* | 11/2007 | Handrosch | A61K 8/0266 428/403 |
| 2008/0038494 | A1* | 2/2008 | Midgley | C09K 11/574 428/34.1 |
| 2008/0248255 | A1* | 10/2008 | Argoitia | C09D 5/29 428/168 |
| 2009/0093551 | A1* | 4/2009 | Bhatia et al. | 514/773 |
| 2010/0224831 | A1 | 9/2010 | Woo et al. | |
| 2010/0290044 | A1* | 11/2010 | Lee | H01M 6/52 356/402 |
| 2010/0295287 | A1* | 11/2010 | Reichert | C09B 67/009 283/70 |
| 2012/0027993 | A1* | 2/2012 | Schmid | C09D 5/28 428/141 |
| 2012/0080878 | A1* | 4/2012 | Kecht | B42D 25/00 283/85 |
| 2012/0091701 | A1* | 4/2012 | Krueger | C09D 7/68 283/57 |
| 2012/0093935 | A1* | 4/2012 | Dembski | C09K 11/7739 424/490 |
| 2012/0193578 | A1* | 8/2012 | Pan | C09K 11/623 252/301.6 F |
| 2013/0102545 | A1* | 4/2013 | Gao et al. | 514/20.9 |
| 2013/0343997 | A1 | 12/2013 | Kennedy et al. | |
| 2014/0131288 | A1* | 5/2014 | Gu et al. | 210/748.14 |
| 2015/0235745 | A1* | 8/2015 | Choe | H01F 1/26 427/127 |

FOREIGN PATENT DOCUMENTS

| | | |
|---|---|---|
| RU | 2254354 | 6/2005 |
| RU | 2470792 | 12/2012 |
| WO | 86/03768 | 7/1986 |
| WO | 2007/036682 | 4/2007 |
| WO | 2012/083133 | 6/2012 |
| WO | 2012/155269 | 11/2012 |

OTHER PUBLICATIONS

Yi-Ying Lu et al., "Long-lasting near-infrared persistent luminescence from—GaO:Crnanowire assemblies", Journal of Luminescence, Elsevier BV North-Holland, NL., vol. 131, No. 12, Jul. 4, 2011, pp. 2784-2787.
Zuoqui Liang et al., "Enhancement of green long lasting phosphorescence in CaSnO3:Tb3+ by addition of alkali ions", Physica B: Condensed Matter, vol. 412, Dec. 20, 2012, pp. 36-40.
Theses n°5694 (2013) EPFL, Usawadee Sakulkhu, "Preparation of coated nanoparticles and investigation of their behavior in biological environment".
International Search Report in respect to International Application No. PCT/EP2014/078388, dated Mar. 17, 2015.
K. Sue et al., "Ultrafast hydrothermal synthesis of Pr-doped Cao. 6Sr0. 4TiO3 red phosphor nanoparticles using corrosion resistant microfluidic devices with Ti-lined structure under high-temperature and high-pressure conditions", Chemical Engineering Journal, 239, 2014, pp. 360-363.
C. Chang et al., "Eu2+ activated long persistent strontium aluminate nano scaled phosphor prepared by precipitation method", Journal of Alloys and Compunds, 415, 2006, pp. 220-224.
Wei Li et al., "Extension of the Stoeber Method to Construct Mesoporous SiO2 and TiO2 Shells for Uniform Multifunctional Core-Shell Structures", Advanced Materials, 25, 2013, pp. 142-149.
M. Chastellain et al., "Particle size investigations of a multistep synthesis of PVA coated superparamagnetic nanoparticles", Journal of Colloid an Interface Science, 278, 2004, pp. 353-360.
A. Petri-Fink, "Development of functionalized superparamagnetic iron oxide nanoparticles for interaction with human cancer cells", Biomaterials, 26, 2005, pp. 2685-2694.
Reju Thomas et al., "Magnetic Iron Oxide Nanoparticles for Multimodal Imaging and Therapy of Cancer", International Journal of Molecular Sciences, 14, 2013, pp. 15910-15930.
Hiroaki Mamiya, "Recent Advances in Understanding Magnetic Nanoparticles in AC Magnetic Fields and Optimal Design for Targeted Hyperthermia", Journal of Nanomaterials, Article ID 752973, 2013.
J. Lodhia et al., "Development and use of iron oxide nanoparticles (Part 1): Synthesis of iron oxide nanoparticles for MRI", Biomedical Imaging and Intervention Journal; 2010; pp. 1-11.
Eeckhout et al., "Persistent Luminescence in $EU^{2+}$-Doped Compounds: A Review", Materials, vol. 3; Apr. 6, 2010; pp. 2536-2566.
Eeckhout et al., "Persistent Luminescence in Non-$EU^{2+}$-Doped Compounds: A Review", Materials, vol. 6; Jul. 12, 2013; pp. 2789-2818.
Noto et al., "Afterglow enhancement with $In^{3+}$codoing in $CaTiO_3:Pr^{3+}$ red phosphor", Powder Technology, 237; Jan. 24, 2013; pp. 141-146.
Chen et al., "Enhanced luminescence properties of $CaTiO_3:Pr^{3+}$ phosphor with additon of $SiO_2$ by solid-state reaction", Spectrochimica Acta Part A: Moleculer and Biomoleculer Spectroscopy, 127; Feb. 25, 2014; pp. 256-260.
Russian office action and Search Report in counterpart Russian Application No. 2016129506, dated Oct. 17, 2017 (and English language translation of Relevant Excerpt).
Chinese office action and Search Report in counterpart Chinese Application No. 201480075925.0 dated Aug. 2, 2017 (and English language translation).

* cited by examiner

THERMOLUMINESCENT COMPOSITE PARTICLE AND MARKING COMPRISING SAME

CROSS-REFERENCE TO RELATED APPLICATION

The present application claims the benefit under 35 U.S.C. § 119(e) of U.S. Provisional Application No. 61/919,037 filed Dec. 20, 2013 and the priority under 35 U.S.C. § 119(a) of International Application No. PCT/EP2013/077823 filed Dec. 20, 2013, the disclosures of which are expressly incorporated by reference herein in their entireties.

BACKGROUND OF THE INVENTION

1. Field of the Invention

The present invention relates to a composite particle which comprises at least one superparamagnetic portion or core and at least one thermoluminescent portion which comprises a doped ceramic material, a marking comprising a plurality of composite particles and to the use of the marking for the identification and/or authentication of an article provided with the marking.

2. Discussion of Background Information

Counterfeiting is no longer a national or a regional problem but a worldwide problem which has an impact not only on manufacturers but also on the consumer. Counterfeiting is a significant problem with goods like clothes and watches but becomes even more serious when it affects medicines and drugs. Each year thousands of people around the world die because of counterfeit drugs. Counterfeiting has also an impact on government revenues in that it affects the collection of taxes for, e.g., cigarettes and alcohol because of the existence of a black market where it is impossible to track and trace counterfeit (smuggled, diverted, etc.) products with no valid tax stamps.

Many solutions have been proposed to make counterfeiting impossible or at least very difficult and/or costly, for example RFID solutions and the use of invisible inks or mono-dimensional code or bi-dimensional code as unique identifier to avoid or at least to limit drastically the existence of fake, diversion and/or counterfeit. Despite the fact that these solutions are useful, also counterfeiters now have access to many advanced technologies that allows them to reproduce or to mimic existing security device which sometimes are presented as unique identifier.

In view of the foregoing, there remains a need to improve the security and avoid faking, diversion or counterfeiting of goods, items or packaging containing valuable products, which must be fulfilled. There also is a need to make sure consumers are provided with genuine products, but very often it also is important in some developing countries to save people from death caused by using fake medicines. There is then a crucial need to be fulfilled to provide unique identifiers useful for authentication, able to provide track and trace info nation or identification which remains robust and provides tamperproof properties.

SUMMARY OF THE EMBODIMENTS

The present invention provides a composite particle for use in a marking. The particle comprises at least one superparamagnetic portion and at least one thermoluminescent portion.

In one aspect of the particle, the thermoluminescent portion thereof may comprise (or consist of) a doped ceramic material.

In another aspect, the composite particle may comprise (a) a superparamagnetic core that is at least partially (and preferably substantially completely) surrounded by (b) a thermoluminescent material in the form of a (preferably substantially continuous) shell or of aggregated thermoluminescent particles comprising (or consisting of) a ceramic material doped with one or more ions selected from transition metal ions and rare earth metal ions. Substantially as used according to the invention means preferably surrounded by at more than 95% of the surface of the core by the thermoluminescent material or the shell being preferably continuous at more than 95% of the surface.

In yet another aspect, the superparamagnetic portion or core of the composite particle may comprise (or consist of) $Fe_3O_4$ and/or the ceramic material may comprise at least one metal and at least one element selected from O, N, S, and P. For example, the ceramic material may comprise at least O and/or S.

In a still further aspect of the composite particle of the present invention, the ceramic material may comprise $Ga_2O_3$ and/or the one or more doping ions may comprise at least one ion selected from the rare earth metal ions, for example, one or more of $Eu^{2+}$, $Eu^{3+}$, $Dy^{3+}$, $Pr^{3+}$, $Sm^{3+}$, $Tb^{3+}$, $Ce^{3+}$, $Ce^{2+}$, $Dy^{3+}$, $Er^{3+}$ and $Tm^{3+}$.

In another aspect, the one or more doping ions may comprise at least two rare earth metal ions and/or at least one doping ion may be selected from a transition metal ion such as $Cr^{3+}$, $Mn^{2+}$ and $Ti^{3+}$.

In another aspect of the composite particle, the largest dimension (e.g., diameter in the case of a spherical particle) of the superparamagnetic portion or core may be from 5 nm to 20 nm, e.g., from 10 nm to 20 nm, more preferably from 10 nm to 15 nm and/or the thickness of the thermoluminescent material may be from 10 nm to 100 nm.

In another aspect, the composite particle of the present invention may further comprise a thermoconductive material that separates the superparamagnetic core or portion thereof from the doped ceramic material. For example, the thermoconductive material may be arranged as a layer or connector between the superparamagnetic portion and the thermoluminescent portion of a composite particle and/or may comprise one or more materials which (1) are thermoconductive, (2) do not interfere with the interaction between an external magnetic field and the superparamagnetic material, (3) are optically transparent for radiation in the UV-Vis and NIR ranges and preferably, (4) can readily be synthesized by processes such the sol-gel process, such as, e.g., $SiO_2$, $TiO_2$, and polymethylmethacrylate, in particular $SiO_2$. The thermoconductive material (layer) may, for example, have a thickness of from 5 nm to 600 nm, e.g., from 10 nm to 600 nm, preferably from 10 nm to 300 nm, more preferably from 10 nm to 200 nm, even more preferably from 10 nm to 100 nm.

The present invention also provides a plurality of composite particles as set forth above (including the various aspects thereof). For example, the plurality of composite particles may comprise at least two composite particles which differ with respect to at least one of the superparamagnetic portion or core, the doped ceramic material and, optionally, the thermoconductive material and/or may comprise at least two composite particles which differ with respect to the thickness of the thermoluminescent shell or the amount and/or concentration of thermoluminescent aggregate particles and/or with respect to the thickness of the (e.g., layer of) thermoconductive material and/or may exhibit at least two different particle size distributions.

The present invention also provides a marking which comprises a plurality of composite particles as set forth above. For example, the marking may be in the form of at least one of an image, a picture, a logo, indicia, a cloud of dots, randomly distributed dots, one or more glyphs and a pattern representing a code selected from one or more of a 1-dimensional barcode, a stacked 1-dimensional barcode, a 2-dimensional barcode, a 3-dimensional barcode, and a data matrix.

The present invention also provides an article that has thereon the marking of the present invention as set forth above. For example, the article may be or may comprise at least one of a label, packaging, a cartridge, a container or a capsule that contains foodstuffs, nutraceuticals, pharmaceuticals or a beverage, a banknote, a credit card, a stamp, a tax label, a security document, a passport, an identity card, a driver's license, an access card, a transportation ticket, an event ticket, a voucher, an ink-transfer film, a reflective film, an aluminum foil, and a commercial good.

The present invention also provides an ink for providing an article with a marking. The ink comprises a plurality of composite particles according to the present invention as set forth above and a carrier for the composite particles.

The present invention also provides a method of providing an article with a marking. The method comprises using the ink of the present invention as set forth above for providing the marking.

The present invention also provides a method of identifying and/or authenticating an article that is provided with a marking according to the present invention as set forth above. The method comprises the following steps:
  (i) irradiating the marking with (preferably electromagnetic) radiation to cause the composite particles to re-emit some of the irradiated energy in the form of radiation (at a wavelength that is characteristic for the thermoluminescent portion);
  (ii) subjecting the irradiated marking to an oscillating magnetic field of predetermined strength and frequency for a predetermined period of time to cause the superparamagnetic material to heat up; and
  (iii) detecting the intensity of the thermoluminescence emitted by the marking at a predetermined wavelength during the predetermined period of time of step (ii) to obtain the variation of the intensity of the thermoluminescence as a function of time (iv) optionally after step (iii) pursuing the detection of the luminescence intensity after the magnetic field is switched off.

In one aspect, the method may further comprise:
comparing the variation of the intensity of thermoluminescence obtained in step (iii) with the variation of the intensity of the thermoluminescence of composite particles used for making the marking (i.e., a reference sample) that had previously been determined under conditions identical to those used in steps (i) and (ii).

In another aspect of the method, the radiation used in step (i) may be in the UV or visible range and/or the wavelength of the radiation re-emitted in step (i) may be in the visible range or the Near Infrared (NIR) range.

In yet another aspect, the method may further comprise the determination of the intensity of the radiation re-emitted in step (i). For example, the intensity of the radiation re-emitted in step (i) may be compared to the intensity of the radiation emitted by the composite particles used in the marking (i.e., a reference sample) which had previously been determined under identical conditions.

The present invention also provides an apparatus for carrying out the method of the present invention as set forth above. The apparatus comprises (1) a radiation source (e.g., a UV lamp or a lamp that emits radiation in the visible wavelength range) for use in step (i), (2) a device that is capable of generating an oscillating magnetic field for use in step (ii) and (3) a device that is capable of detecting the intensity of the thermoluminescence for use in step (iii).

In one aspect of the apparatus, (1) and (3) may be combined in a single unit. In this case, the apparatus may further comprise (4) an optical fiber which is connected to the single unit and is capable of providing the marking with actinic radiation from (1) and of providing (3) with thermoluminescence emitted by the marking.

BRIEF DESCRIPTION OF THE DRAWINGS

The present invention is further described in the detailed description which follows, in reference to the drawings wherein.

DETAILED DESCRIPTION OF THE EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

As used herein, the singular forms "a," "an," and "the" include the plural reference unless the context clearly dictates otherwise. For example, reference to "a superparamagnetic material" would also mean that mixtures of two or more superparamagnetic materials can be present unless specifically excluded.

Except where otherwise indicated, all numbers expressing quantities of ingredients, reaction conditions, etc. used in the instant specification and appended claims are to be understood as being modified in all instances by the term "about." Accordingly, unless indicated to the contrary, the numerical parameters set forth in the specification and claims are approximations that may vary depending upon the desired properties sought to be obtained by the present invention. At the very least, each numerical parameter should be construed in light of the number of significant digits and ordinary rounding conventions.

Additionally, the disclosure of numerical ranges within this specification is considered to be a disclosure of all numerical values and ranges within that range. For example, if a range is from about 1 to about 50, it is deemed to include, for example, 1, 7, 34, 46.1, 23.7, 50 or any other value or range within the range.

The various embodiments disclosed herein can be used separately and in various combinations unless specifically stated to the contrary.

The present invention features the concurrent use of a superparamagnetic material and a thermoluminescent material for marking, identification and/or authentication purposes. Superparamagnetism is a form of magnetism which appears in small ferromagnetic or ferrimagnetic nanoparticles. In sufficiently small nanoparticles, magnetization can randomly flip direction under the influence of temperature. In the absence of an external magnetic field, the magnetization of the nanoparticles appears to be on the average zero. In this state, an external magnetic field is able to magnetize the nanoparticles, similarly to a paramagnet. However, their magnetic susceptibility is much larger than that of paramagnets. Superparamagnetism occurs in nanoparticles which are single-domain, i.e. are composed of a single magnetic domain. This is usually the case when the diameter of the nanoparticles is in the range of from 1 nm to 20 nm, depending on the material the nanoparticles consist of. In this condition, the magnetization of the nanoparticles can be considered to be a single giant magnetic moment, the sum of all the individual magnetic moments carried by the atoms of the nanoparticle. When an external magnetic field is applied to an assembly of superparamagnetic nanoparticles, their magnetic moments tend to align along the applied field, leading to a net magnetization.

Thermoluminescence is a form of luminescence that is exhibited by certain crystalline materials, when previously absorbed energy from electromagnetic radiation or other ionizing radiation is re-emitted as light upon heating of the material. In a thermoluminescent material such as a ceramic doped with a transition metal/rare earth metal ion that has been irradiated with actinic radiation such as UV radiation or radiation in the visible range of the electromagnetic spectrum electronic exited states are created. These states are trapped for extended periods of time by imperfections (caused by the dopant) in the crystal lattice, which imperfections interrupt the normal intermolecular or inter-atomic interactions in the crystal lattice. Quantum-mechanically, these states are stationary states which have no formal time dependence; however, they are not stable energetically. Heating the material enables the trapped states to interact with lattice vibrations, to rapidly decay into lower-energy states, causing the emission of photons (radiation) in the process. The intensity of the radiation is dependent on the temperature of the material. If the material is heated at a constant heating rate the intensity of the emitted radiation will first increase with temperature and then decrease again, giving rise to a "glow curve" upon plotting the intensity of the emitted radiation versus the temperature of the thermoluminescent material. The shape and position of the glow curve or part thereof are dependent on the ceramic (host) material (including defects in the material such as, e.g., oxygen vacancies) and its dopant.

According to the present invention, the heating of the doped ceramic material is accomplished indirectly by providing the heat through a superparamagnetic material (e.g., the core of a core-shell particle) that is subjected to an oscillating magnetic field (and thereby caused to heat up) for a predetermined period of time. The glow curve or part thereof which is obtained by plotting the intensity of the radiation emitted by the thermoluminescent material versus the time of applying the oscillating magnetic field (heating) is dependent not only on the parameters associated with the doped ceramic material but also on the parameters associated with the superparamagnetic material. This makes it possible to use particles which comprise both of these materials for making markings that are almost impossible to duplicate without knowledge of this plurality of parameters.

The composite particle of the present invention comprises at least one superparamagnetic portion (e.g. a core) and at least one thermoluminescent portion (e.g., a shell or an aggregate of thermoluminescent particles which reproducibly contribute to the "glow curve" of the thermoluminescent material and are randomly distributed around the superparamagnetic portion). The thermoluminescent portion preferably comprises (or consists of) one or more (e.g., two or three) doped ceramic materials.

The composite particle will often be present in the form of a core-shell particle, with the core comprising (or consisting of) a superparamagnetic material and the shell comprising (or consisting of) a ceramic material that has been doped with at least one transition metal ion and/or at least one rare earth metal ion. In this regard it is to be noted that the term "rare earth metal" as used herein and in the appended claims is meant to include Y, Sc, La and the lanthanides (Ce to Lu). In this regard, it is to be appreciated that a composite particle according to the present invention such as a core-shell composite particle does not have to be (substantially) spherical. For example, the composite particle may be of a rod-like shape or any other non-spherical shape, as long as it comprises a superparamagnetic portion (e.g., core) and a thermoluminescent portion (e.g., a shell or an aggregate of particles randomly distributed around the superparamagnetic portion).

The superparamagnetic portion or core of the composite particle comprises (or consist of) a superparamagnetic material (or combinations of two or more superparamagnetic materials). Examples thereof include iron oxide such as $Fe_3O_4$ (also known as magnetite or ferric oxide), metallic Fe, metallic Co, metallic Ni, metal alloys (e.g., FeCo, FeNi, FePt, SmCo). Preferred are superparamagnetic nanoparticles based upon iron oxide. These are commonly referred to as superparamagnetic iron oxide (SPIO) particles and methods for the fabrication of SPIO nanoparticles is known to those of skill in the art (for example, see Lodhia et al. Development and use of iron oxide nanoparticles (Part I): Synthesis of iron oxide nanoparticles for MRI. Biomedical Imaging and Intervention Journal, 6(2):e12, 2010).

The ceramic material will often comprise, in addition to one or more metals (including main group, transition and/or rare earth metals) and, optionally, B and/or Si, one or more elements selected from O, N, S, P, in particular O, optionally in combination with one or more of S and P. A preferred and non-limiting example of a ceramic material for use in the present invention is $Ga_2O_3$. Other non-limiting examples of ceramic materials which are suitable for use in the present invention include $Ba_2MgSi_2O_7$, $Ba_2Si_3O_8$, $Ba_2SiO$, $Ba_2ZnSi_2O_7$, $Ba_5Si_8O_{21}$, $BaSi_2O_5$, $BaSiO_3$, $CaGd_2Si_2O_7$, $Li_2CaSiO_4$, $MgSr_2Si_2O_7$, $NaLaSiO_4$, $Y_2SiO_5$, $BaAl_{10}MgO_{17}$, $BaAl_{12}O_{19}$, $BaHfO_3$, $CaHf_3$, $CaAl_2O_4$, $SrAl_2O_4$, $BaAl_2O_4$, $GdSc_2Al_3O_{12}$, $Gd_3Y_3Al_{10}O_{24}$, $La_2O_3$, $LaAlO_3$, $SrHfO_3$, $YAlO_3$, $Ba_2B_5O_9Cl$, $Ba_2Ca(BO_3)_2$, $Ba_3Gd(BO)_3$, $Ca_4YO(BO_3)_3$, $CaLaB_7O_{13}$, $CaYBO_4$, $GdB_3O_6$, $GdBO_3$, $LaB_3O_6$, $LaBO_3$, $LaMgB_5O_{10}$, $Li_6Gd(BO_3)_3$, $Li_6Y(BO_3)_3$, $LuBO_3$, $ScBO_3$, $YAl_3B_4O_{12}$, $YBO_3$, $AgGd(PO_3)_4$, $Ba_2P_2O_7$, $Ba_3(PO_4)_2$, $Ba_3B(PO_4)_3$, $Ba_3P_4O_{13}$, $Ba_5(PO_4)_3F$, $BaKPO_4$, $BaP_2O_6$, $Ca_5(PO_4)_3F$, $CaBPO_5$, $CeP_5O_{14}$, $CsGd(PO_3)_4$, $CsLuP_2O_7$, $CsYP_2O_7$, $K_3Lu(PO_4)_2$, $KGd(PO_3)_4$, $LuP_2O_7$, $KYP_2O_7$, $LiCaPO_4$, $LiGd(PO_3)_4$, $LuPO_4$, $NaBaPO_4$, $NaGd(PO_3)_4$, $NaLuP_2O_7$, $RbLuP_2O_7$, $RbYP_2O_7$, $Sr_5(PO_4)_3F$, $Gd_2O_2S$, $Gd_2S_3$, $Lu_2S_3$, $La_2O_2S$, $CaSnO_3$, $ZnGa_2O_4$, $MgGa_2O_4$, $CaTiO_3$, $ZnTa_2O_6$.

The doping ions are preferably selected from one or more of $Eu^{2+}$, $Eu^{3+}$, $Dy^{3+}$, $Pr^{3+}$, $Sm^{3+}$, $Tb^{3+}$, $Ce^{3+}$, $Ce^{2+}$, $Er^{3+}$ and $Tm^{3+}$ and/or one or more of $Cr^{3+}$, $Mn^{2+}$ and $Ti^{3+}$. Of course, any other rare earth metal ion (e.g., lanthanide ion) and any other transition metal ion may be used as well for the purposes of the instant invention as long as it is capable of providing thermoluminescence in combination with the selected ceramic (host) material. A specific non-limiting example of a doped ceramic material that is suitable for use as the thermoluminescent portion of the composite particle of the present invention is $Ga_2O_3:Cr^{3+}$.

The largest (average) dimension (e.g., diameter) of the superparamagnetic portion or core of the composite particle of the present invention will usually be at least 5 nm, e.g., at least 10 nm, and will usually be not higher than 50 nm, e.g., not higher than 30 nm, not higher than 20 nm, or not higher than 15 nm.

The (average) thickness of the thermoluminescent material, for example if present in the form of a shell, will usually be not less than 5 nm, e.g., not less than 10 nm, and will usually be not higher than 200 nm, e.g., not higher than 100 nm, not higher than 75 nm, not higher than 50 nm, not higher than 40 nm, or not higher than 25 nm.

In a preferred embodiment of the composite particle of the present invention, the particle additionally comprises a thermoconductive material that separates the superparamagnetic portion or core from the thermoluminescent portion (e.g., a thermoluminescent shell). For example, the thermoconductive material can be present in the form of a layer between the core and the shell of a core-shell particle or a connector between the a superparamagnetic core and an aggregate of thermoluminescent particles. Alternatively, it can also be present, for example, as a matrix in which several (e.g. two, three, four or more) superparamagnetic cores are embedded and which is surrounded, at least partially, by the thermoluminescent material.

The thermoconductive material can be inorganic or organic and is advantageously selected from materials which (1) are thermoconductive, (2) do not interfere with the interaction between an external magnetic field and the superparamagnetic material, (3) are optically transparent for radiation in the UV-Vis and NIR range (so as to not interfere with the excitation of the thermoluminescent material or the emission of radiation by the thermoluminescent material) and preferably, (4) can readily be synthesized by processes such as the sol-gel process. Examples of corresponding materials include inorganic oxides such as, e.g., $SiO_2$ and $TiO_2$ and organic polymers such as, e.g., polymethylmethacrylate. A preferred thermoconductive material for use in the present invention is $SiO_2$. For example, in the case of a silica coating around the superparamagnetic particles, tetraethoxysilane may be added to a suspension of the particles, followed by hydrolysis, which results in a suspension of silica-coated superparamagnetic particles. Other suitable sources of silica include sodium silicate, potassium silicate, lithium silicate, aluminum silicate, zirconium silicate, calcium silicate, and silicic acid.

The (average) thickness of the thermoconductive material, for example if present in the form of a layer between a superparamagnetic portion and a thermoluminescent portion, will often be not lower than 5 nm, e.g., not lower than 10 nm, or not lower than 20 nm, and will often (although not necessarily) be not higher than 600 nm, e.g., not higher than 500 nm, not higher than 200 nm, or not higher than 100 nm.

The presence of the thermoconductive material in the composite particle of the present invention makes it possible to influence the "glow curve" (i.e., the curve obtained by plotting the intensity of radiation emitted by the thermoluminescent material versus the time of subjecting the superparamagnetic material to an oscillating magnetic field) not only by variables associated with the superparamagnetic material (e.g., composition of material and size and number of superparamagnetic cores) and associated with the thermoluminescent material (e.g., composition of ceramic material, nature and concentration of dopant ion(s), thickness of material), but also by variables associated with the thermoconductive material (e.g., composition of thermoconductive material, thickness of layer). In particular, since the thermoconductive layer separates the superparamagnetic material (i.e., the heating source) from the thermoluminescent material (the material to be heated) both the thermal conductivity and the thickness of the thermoconductive material will affect the rate at which the thermoconductive material is heated once application of the oscillating magnetic field has commenced and thus, the onset of radiation and the slope of the increase (and decrease) of the intensity of the radiation emitted by the thermoluminescent material.

Figure 1:
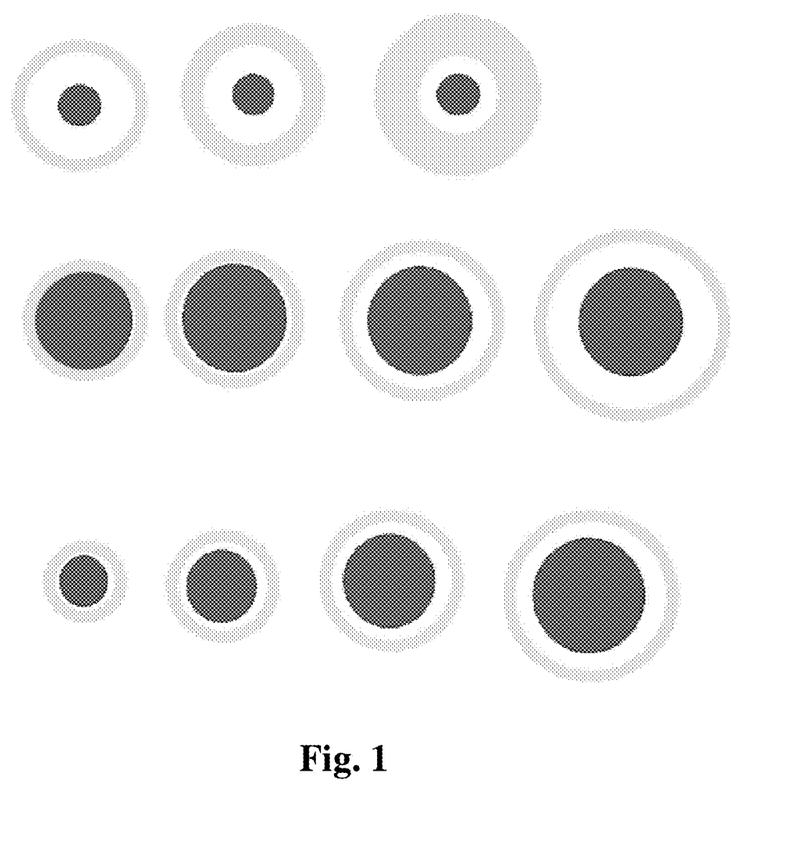
FIG. 1 schematically shows different possible structures of a core-shell composite particle according to the present invention.

FIG. 1 schematically shows several possible structures of a (spherical) core-shell particle according to the present invention. In FIG. 1 the innermost circle represents the superparamagnetic core and the outermost circle represents the thermoluminescent material. The white circle, if present, represents the thermoconductive material.

As is apparent from the foregoing, the glow curve and other characteristics of a composite particle according to the present invention can be influenced by a host of variables relating to the superparamagnetic portion, the thermoluminescent portion and, optionally, also to the thermoconductive portion thereof, providing a virtually unlimited number of different particles which are distinguishable based on their properties and in particular, their glow curve upon application of an oscillating magnetic field of predetermined strength and frequency thereto.

Further, if a plurality of composite particles according to the present invention is present (as is the case of a marking), there are even further possibilities of influencing, for example, the glow curve of the thermoluminescent material, thereby increasing the number of possible variations even further. For example, the plurality of particles may comprise two or more kinds of composite particles which differ from each other with respect to at least one of the superparamagnetic material, the doped ceramic material and, optionally, the thermoconductive material used for the production thereof. Alternatively or in addition thereto, the plurality of particles may have been made from the exactly the same materials, but two or more groups of particles may differ with respect to at least one of the (average) size of the superparamagnetic material, the (average) thickness of the thermofluorescent (e.g., doped ceramic) material and, optionally, the (average) thickness of the thermoconductive material (e.g., layer). Even further, these particles may be present in different particle size distributions. In this regard, it is to be appreciated that due to synthetic constraints, it is not possible to produce particles which have exactly the same dimensions of, e.g., superparamagnetic portion, the thermoluminescent portion and, optionally, the thermoconductive portion. Accordingly, a plurality of composite particles of the present invention will inevitably comprise particles whose respective dimensions are scattered to a certain extent around average values of each parameter (thereby providing a glow curve as an average of the plurality of particles). Merely by way of example, in a given sample of particles the size (diameter) of the core may vary by up to 20%, preferably not more than 10% (for example, 10 nm+/−1 nm), the thickness of the luminescent shell or the aggregate of thermoluminescent particles may vary by up to 35%, preferably not more than 25% (e.g., 20 nm+/−5 nm), and the thickness of a layer of thermoconductive material, if present, may vary by up to 20%, preferably not more than 10% (e.g., 50 nm+/−5 nm).

A marking which comprises a plurality of composite particles of the present invention may be present in many different forms. By way of non-limiting example, the marking may be in the form of at least one of an image, a picture, a logo, indicia, a cloud of dots, randomly distributed dots, one or more glyphs and a pattern representing a code selected from one or more of a 1-dimensional barcode, a stacked 1-dimensional barcode, a 2-dimensional barcode, a 3-dimensional barcode, and a data matrix.

An article which can be provided with a marking of the present invention can be present in many different forms as well. For example, the article may be or may comprise at least one of a label, packaging, a cartridge, a container or a capsule that contains foodstuffs, nutraceuticals, pharmaceuticals or a beverage, a banknote, a credit card, a stamp, a tax label, a security document, a passport, an identity card, a driver's license, an access card, a transportation ticket, an event ticket, a voucher, an ink-transfer film, a reflective film, an aluminum foil, and a commercial good.

An ink which can be used for making a marking of the present invention can be any ink that is suitable for making a marking on an article and comprises a plurality of composite particles as set forth above and allows the detection of thermoluminescence. The ink may also comprise additional components which can be used for identification/authentication purposes, as long as these components do not interfere with the detection of radiation and in particular, thermoluminescence emitted by the composite particles.

The method of making (providing an article with) the marking of the present invention is not limited, as long as it can accommodate an ink which contains the composite particles of the present invention.

The marking of the present invention may, for example, be formed by digital printing. However, the marking may also be formed by a conventional printing method or any other method that allows the production of a marking. An exemplary method for producing the marking is ink jet printing (for example, continuous ink jet printing, drop-on-demand ink-jet printing, or valve-jet printing). The industrial ink-jet printers, commonly used for numbering, coding and marking applications on conditioning lines and printing presses, are particularly suitable for this purpose. Preferred ink-jet printers include single nozzle continuous ink-jet printers (also called raster or multi level deflected printers) and drop-on-demand ink-jet printers, in particular valve-jet printers. Other conventional techniques such as offset, rotogravure, screen printing, letterpress, flexography, intaglio, etc. can also be used and are known by the skilled on in the art.

A method of identifying and/or authenticating an article that has been provided with a marking according to the present invention may comprise the following steps:
(i) irradiating the marking with (preferably electromagnetic) radiation (e.g., radiation in the UV or visible range of the electromagnetic spectrum) to cause the composite particles to emit radiation at a wavelength that is characteristic for the thermoluminescent portion;
(ii) subjecting the irradiated marking to an oscillating magnetic field of predetermined strength (e.g., in the range of from 1 G to 500 G or even lower, depending on the specific material used for the superparamagnetic core and the size thereof) and predetermined frequency (e.g., in the range of from 1 kHz to 500 kHz or even lower, depending on the specific material and size of the superparamagnetic core) for a predetermined period of time (e.g., in the range of from 1 s to 30 s) to cause the superparamagnetic material to heat up; and
(iii) detecting the intensity of the thermoluminescence emitted by the marking at a predetermined wavelength during the predetermined period of time of step (ii) to obtain the variation of the intensity of the thermoluminescence as a function of time ("glow curve")
(iv) optionally after step (iii) pursuing the detection of the luminescence intensity after the magnetic field is switched off.

In order to reach the magnetic field strength mentioned above over a surface where the marking has been applied (without being able to access both sides of the surface), it is required to have a special configuration of the magnet. This represents a difficulty which can be solved by using a torroidal magnet with a very small air gap to allow the fringing magnetic field to penetrate the marking on the surface and to reach the necessary magnetic field strength. In this preferred configuration, the small size of the air gap represents a complication for the irradiation and also for the collection of the radiated thermoluminescence. That would require the use of a complex optical scheme, with micro lenses and mirrors in order to irradiate efficiently through the small air gap and also to collect enough thermoluminescence signal.

The predetermined wavelength at which the thermoluminescence (and optionally also the radiation emitted in step (i)) is detected depends on the doping ion(s) and the ceramic (host) material. For example, if the material is $Ga_2O_3:Cr^{3+}$ the thermoluminescence will usually be detected at 720+/−10 nm, whereas when the material is $CaSnO_3:Tb^{3+}$ the thermoluminescence will usually be detected at 550+/−10 nm.

In a preferred embodiment, the method of the present invention may further comprise a comparison of the variation of the intensity of the thermoluminescence obtained in step (iii) with the variation of the intensity of the thermoluminescence of composite particles used for making the marking (i.e., a reference sample) that had previously been determined under conditions identical to those used in steps (i) and (ii). If the variations are identical, this is a very strong indication, if not conclusive evidence, that the marking is the original marking (i.e., has not been duplicated).

In another preferred embodiment, the method may further comprise the determination of the intensity of the radiation emitted in step (i) at the predetermined wavelength. For example, the intensity of the radiation in step (i) may be compared to the intensity of the radiation emitted by the composite particles used in the marking (reference sample) that had previously been determined on a reference sample under identical conditions, preferably in the form of the ratio of the intensity of the radiation emitted in step (i) and the intensity of the radiation emitted after a fixed point in time after the commencement of the application of the oscillating magnetic field. If the ratios are identical, this is further evidence that the marking is the original marking.

An apparatus for carrying out the method of the present invention may comprise a radiation source for use in step (i) such as, e.g. a lamp that emits radiation in the UV and/or visible range, a device for generating an oscillating magnetic field for use in step (ii), and a device for detecting the intensity of the thermoluminescence for use in step (iii) (and optionally also the intensity of the re-emitted radiation in step (i)).

In a preferred embodiment of the apparatus, the source of radiation and the device for detecting the intensity of radiation emitted by the marking are combined in a single unit. This makes it possible to use a single device such as a single optical fiber which is connected to the unit and is capable of providing the marking with radiation from the source of radiation and of providing the detection device with the thermoluminescence emitted by the marking (the composite particles of the present invention). The use of an optical fiber allows to solve the problem of limited accessibility of the optical measurement area located within the very small air gap need to produce the required magnetic field strength on the marking surface as explained above.

Figure 2:
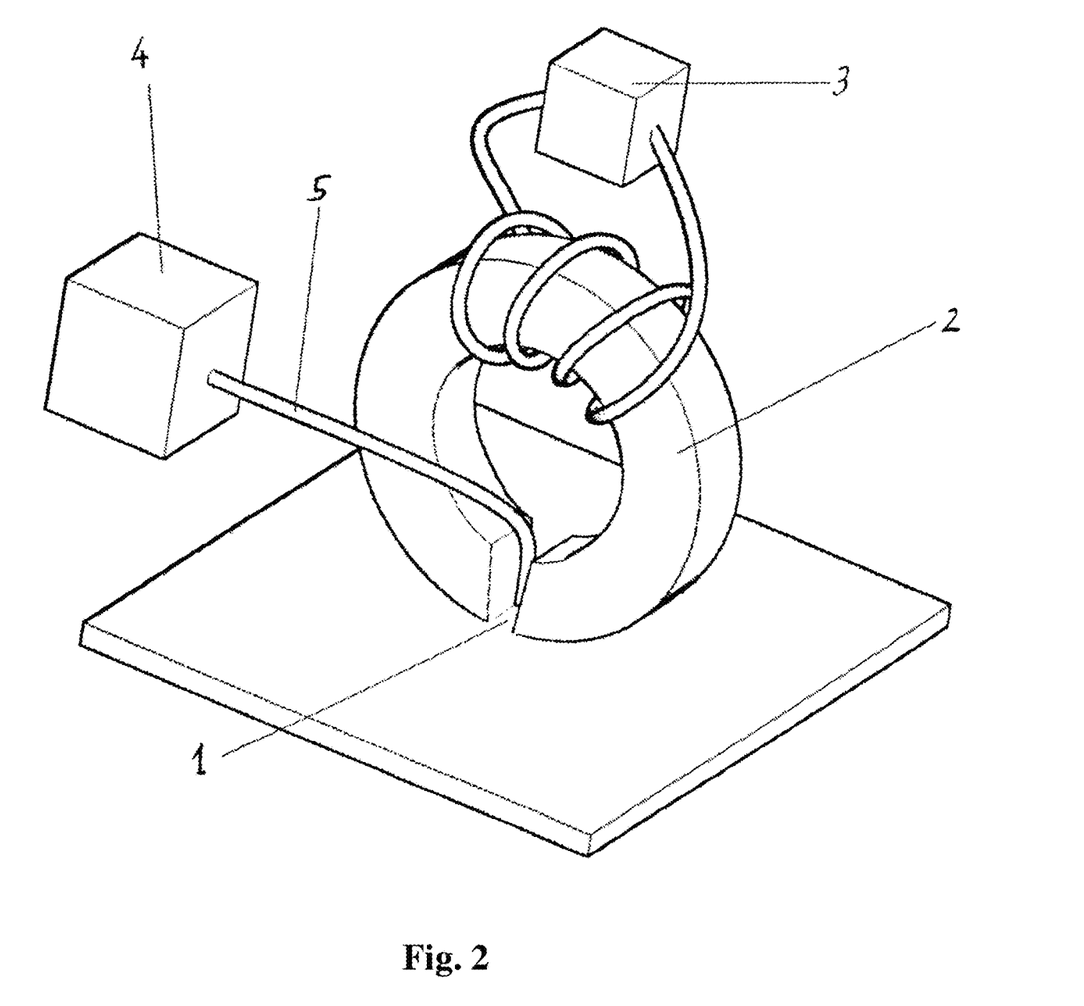
FIG. 2 schematically shows an apparatus for use in a method according to the present invention.

FIG. 2 schematically shows an apparatus for carrying out the method of the present invention. In FIG. 2, reference numeral 1 represents the marking comprising the composite particles of the present invention, 2 represents a magnet with the small air gap located onto the marking to be authenticated, 3 represents an alternating current generator, 4 represents a combined irradiation and detection unit for radiation emitted by the marking and 5 represents a (single) optical fiber which transmits radiation to and from the unit 4 and permit to access the measurement zone through the small air gap.

The synthesis of the composite particle follows the bottom-up approach, whereas the building blocks (superparamagnetic iron oxide nanoparticles and thermoluminescent part) are synthesized separately and are integrated together via sol-gel synthesis.

Superparamagnetic iron oxide nanoparticles with controlled diameters can be obtained via well established procedures as described in:

Journal of Nanomaterials, 2013, Article ID 752973, Hiroaki Mamiya, Recent Advances in Understanding Magnetic Nanoparticles in AC Magnetic Fields and Optimal Design for Targeted Hyperthermia International Journal of Molecular Sciences, 2013, 14, 15910-15930, Reju Thomas and al., Magnetic Iron Oxide Nanoparticles for Multimodal Imaging and Therapy of Cancer Thèse n° 5694 (2013) EPFL, Usawadee Sakulkhu, Preparation of coated nanoparticles and investigation of their behavior in biological environment.

Journal of Colloid and Interface Science 278, 353-360 (2004), Chastellain, M., Petri, A. & Hofmann, H. Particle size investigations of a multistep synthesis of PVA coated superparamagnetic nanoparticles.

Biomaterials 26, 2685-2694 (2005), Petri-Fink, A., Chastellain, M., Juillerat-Jeanneret, L., Ferrari, A. & Hofmann, H. Development of functionalized superparamagnetic iron oxide nanoparticles for interaction with human cancer cells.

Superparamagnetic iron oxide nanoparticles can also be purchased from Sigma Aldrich.

Superparamagnetic core coated with a silica layer is obtained via the well-known sol-gel synthesis, as described in:

Advanced Materials, 2013, 25, 142-149, Wei Li and Dongyuan Zhao, Extension of the Stöber Method to Construct Mesoporous SiO2 and TiO2 Shells for Uniform Multifunctional Core-Shell Structures Moreover, parameters such as, precursor concentration, catalyst concentration, solvent, temperature, pH, agitation and reaction duration, are controlled in order to produce homogeneously distributed nano engineered particles. The silica precursor is tetraethyl orthosilicate (TEOS) and the catalyst is a base such as ammonia ($NH_4OH$). For instance, 10 mg Fe/ml SPION in 5% w/v sodium citrate is mixed with 15 ml of deionized water for 2 min. Then, 20 μl of TEOS diluted in 80 ml of ethanol are added to the previously prepared Fe solution, and stirred for 5 min. After that, 8 ml of ammonia (25% in water) is added into the middle of the flask and the total mixture is stirred over 1 h at room temperature. Finally the particles are centrifuged and washed twice with deionized water. In order to have an enriched superparamagnetic core, the relative concentration of SPION versus TEOS is increased. In order to have particles with different thicknesses of the silica shells, a two step addition of TEOS is realized where in the second addition, the concentrations of TEOS are varied. More details about the synthesis can be found in the following document:

Thèse n° 5694 (2013) EPFL, Usawadee Sakulkhu, Preparation of coated nanoparticles and investigation of their behavior in biological environment.

Electrostatic and other weak interactions enable adsorption of other nanoparticles on the surface of the silica coated SPIONs. In this case, thermoluminescent particles, previously synthesized, are aggregated on the multi SPION core-silica shells. It is possible to increase the electrostatic interaction between the SPION-silica particle and the thermoluminescent particle by functionalizing the SPION-silica surface with (3-aminopropyl) triethoxysilane (APTES), leading to a positively charged surface SPION-silica and by coating with a thin layer of silica the previously synthesized nano sized thermoluminescent particle. The last provides a negatively charged surface of the thermoluminescent part due to the OH groups of surface silanols, and thus favors the aggregation of the thermoluminescent part onto the SPION-silica part. The total core-shell particles are coated with a thin layer of silica. This layer enables further functionalization of the surface for desired applications and maintains the heat transfer within the total composite particle.

In order to aggregate/adsorb the thermoluminescent particles onto the silica coated multi-SPION, the particle size should not exceed 50 nm, preferably 20-30 nm. Several synthetic approaches lead to nano sized powders such as precipitation followed by hydrothermal crystallization and hydrothermal precipitation. These approaches are preferable compared to solid state reactions due to their mild and environment friendly conditions.

The examples for the synthesis of such particles can be found in the following literature:

Chemical Engineering Journal, 239, (2014), 360-363, K. Sue et al., Ultrafast hydrothermal synthesis of Pr-doped $Ca_{0.6}Sr_{0.4}TiO_3$ red phosphor nanoparticles using corrosion resistant microfluidic devices with Ti-lined structure under high-temperature and high-pressure conditions.

Journal of Alloys and Compounds 415, (2006), 220-224, C. Chang, Z. Yuan and D. Mao, $Eu^{2+}$ activated long persistent strontium aluminate nano scaled phosphor prepared by precipitation method.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A composite particle for use in a marking, wherein the composite particle comprises a thermoconductive material matrix comprising two or more superparamagnetic cores embedded therein, each of the two or more superparamagnetic cores consisting of one or more superparamagnetic materials selected from iron oxide, metallic Fe, metallic Co, metallic Ni and metal alloys, and the matrix is surrounded by a thermoluminescent portion present in the form of a shell around the matrix in which the two or more superparamagnetic cores are embedded, or of an aggregate of thermoluminescent particles which are randomly distributed around the matrix in which the two or more superparamagnetic cores are embedded, the thermoluminescent portion consisting of two or more doped ceramic materials, each of the two or more doped ceramic materials being selected from the following: $Ba_2MgSi_2O_7$, $Ba_2Si_3O_8$, $Ba_2SiO$, $Ba_2ZnSi_2O_7$, $Ba_5Si_8O_{21}$, $BaSi_2O_5$, $BaSiO_3$, $CaGd_2Si_2O_7$, $Li_2CaSiO_4$, $NaLaSiO_4$, $BaAl_{10}MgO_{17}$, $BaAl_{12}O_{19}$, $BaHfO_3$, $CaHf_3$, $GdSc_2Al_3O_{12}$, $Gd_3Y_3Al_{10}O_{24}$, $La_2O_3$, $LaAlO_3$, $SrHfO_3$, $Ba_2B_5O_9Cl$, $Ba_2Ca(BO_3)_2$, $Ba_3Gd(BO)_3$, $Ca_4YO(BO_3)_3$, $CaLaB_7O_{13}$, $CaYBO_4$, $GdB_3O_6$, $GdBO_3$, $LaB_3O_6$, $Li_6Gd(BO_3)_3$, $Li_6Y(BO_3)_3$, $YAl_3B_4O_{12}$, $AgGd(PO_3)_4$, $Ba_3(PO_4)_2$, $Ba_3B(PO_4)_3$, $Ba_3P_4O_{13}$, $Ba_5(PO_4)_3F$, $BaKPO_4$, $BaP_2O_6$, $CaBPO_5$, $CeP_5O_{14}$, $CsGd(PO_3)_4$, $CsLuP_2O_7$, $CsYP_2O_7$, $K_3Lu(PO_4)_2$, $KGd(PO_3)_4$, $LuP_2O_7$, $KYP_2O_7$, $LiCaPO_4$, $LiGd(PO_3)_4$, $LuPO_4$, $NaBaPO_4$, $NaGd(PO_3)_4$, $NaLuP_2O_7$, $RbLuP_2O_7$, $RbYP_2O_7$, $Gd_2S_3$, $Lu_2S_3$, $CaSnO_3$, and $ZnTa_2O_6$, each doped with at least one doping ion selected from $Eu^{2+}$, $Eu^{3+}$, $Dy^{3+}$, $Pr^{3+}$, $Sm^{3+}$, $Tb^{3+}$, $Ce^{3+}$, $Ce^{2+}$, $Er^{3+}$, $Tm^{3+}$, $Cr^{3+}$, $Mn^{2+}$, and $Ti^{3+}$, wherein the composite particle has a spherical or rod-like shape, wherein the thermoconductive material comprises one or more of $SiO_2$, $TiO_2$, and polymethylmethacrylate, wherein the two or more doped ceramic materials are selected such that they provide distinct glow curves, wherein a glow curve of each of the two or more doped ceramic materials is obtained by plotting an intensity of radiation emitted by the ceramic material versus time of applying an oscillating magnetic field to the superparamagnetic materials of the composite particle.

2. The composite particle according to claim 1, wherein at least one of the two or more superparamagnetic cores comprises $Fe_3O_4$.

3. The composite particle according to claim 1, wherein the one or more doping ions comprise at least one ion selected from $Eu^{2+}$, $Dy^{3+}$, $Cr^{3+}$ and $Pr^{3+}$.

4. The composite particle according to claim 1, wherein the one or more doping ions comprise at least $Eu^{2+}$ and $Dy^{3+}$.

5. The composite particle according to claim 1, wherein the one or more doping ions comprise at least one ion selected from $Cr^{3+}$, $Mn^{2+}$, and $Ti^{3+}$.

6. The composite particle according to claim 1, wherein the thermoconductive material comprises $SiO_2$.

7. The composite particle according to claim 1, wherein a largest dimension of each of the two or more superparamagnetic cores is from 5 nm to 20 nm, and the thermoluminescent portion has a thickness of from 10 nm to 100 nm.

8. A plurality of composite particles according to claim 1, wherein the plurality of composite particles comprises at least two composite particles which differ with respect to at least one of the superparamagnetic core, the thermoluminescent portion and, optionally, the thermoconductive material.

9. A plurality of composite particles according to claim 8, wherein the plurality of composite particles comprise at least two composite particles which differ with respect to the thickness of the thermoluminescent portion.

10. A plurality of composite particles according to claim 8, wherein the plurality of composite particles exhibit at least two different particle size distributions.

11. A marking which comprises a plurality of composite particles according to claim 1.

12. The marking according to claim 11, wherein at least a part of the marking is in the form of at least one of an image, a picture, a logo, indicia, a cloud of dots, randomly distributed dots, one or more glyphs and a pattern representing a code selected from one or more of a 1-dimensional barcode, a stacked 1-dimensional barcode, a 2-dimensional barcode, a 3-dimensional barcode, a data matrix.

13. An article having thereon the marking according to claim 11.

14. The article of claim 13, wherein the article is or comprises at least one of a label, packaging, a cartridge, a container or a capsule that contains foodstuffs, nutraceuticals, pharmaceuticals or a beverage, a banknote, a credit card, a stamp, a tax label, a security document, a passport, an identity card, a driver's license, an access card, a transportation ticket, an event ticket, a voucher, an ink-transfer film, a reflective film, an aluminum foil, and a commercial good.

15. An ink for making a marking, wherein the ink comprises a plurality of composite particles according to claim 1 and a carrier for the composite particles.

16. A method of providing an article with a marking, wherein the method comprises using the ink according to claim 15 for providing the marking.

17. A method of at least one of identifying and authenticating an article provided with a marking according to claim 11, wherein the method comprises the following steps:

(i) irradiating the marking with radiation to cause the composite particles to emit radiation;

(ii) subjecting the irradiated marking of step (i) to an oscillating magnetic field of predetermined strength and frequency for a predetermined period of time to cause the superparamagnetic material to heat up; and (iii) detecting the intensity of the thermoluminescence emitted by the marking at a predetermined wavelength during the period of time applied in step (ii) to obtain the variation of the intensity of the thermoluminescence as a function of time (iv) optionally after step (iii) pursuing the detection of the luminescence intensity after the magnetic field is switched off.

18. The method according to claim 17, wherein the method further comprises comparing the variation of the intensity of thermoluminescence obtained in (iii) with the variation of the intensity of the thermoluminescence of a reference sample that had previously been determined under conditions identical to those used in steps (i) and (ii).

19. The method according to claim 17, wherein the radiation used in step (i) is in the UV or visible range.

20. The method according to claim 17, wherein the method further comprises determining the intensity of the radiation emitted in step (i).

21. The method according claim 20, wherein the method further comprises comparing the intensity of the radiation emitted in step (i) to the intensity of the radiation emitted by the reference sample that had previously been determined under identical conditions.

22. An apparatus for carrying out the method according to claim 17, wherein the apparatus comprises (1) a radiation source for use in step (i), (2) a device capable of generating an oscillating magnetic field for use in step (ii) and (3) a device capable of detecting the intensity of the thermoluminescence for use in step (iii).

23. The apparatus according to claim 22, wherein (1) and (3) are combined in a single unit.

24. The apparatus according to claim 23, wherein the apparatus further comprises (4) an optical fiber which is connected to the single unit and is capable of providing the marking with radiation emitted by (1) and of providing (3) with thermoluminescence emitted by the marking.

25. A process for marking objects, substrates and/or supports by inkjet printing via the continuous deflected jet technique, by spraying an ink composition according to claim 15 onto these objects.

26. The composite particle according to claim 1, wherein the thermoconductive material comprises polymethylmethacrylate.

\* \* \* \* \*